United States Patent
Abraham et al.

(10) Patent No.: US 12,376,993 B2
(45) Date of Patent: Aug. 5, 2025

(54) CONTROLLING THE TEMPERATURE OF THE CORNEA DURING OPHTHALMIC SURGERY

(71) Applicant: Alcon Inc., Fribourg (CH)

(72) Inventors: Mario Abraham, Burgthann (DE); Michael Wittnebel, Hirschaid (DE)

(73) Assignee: ALCON INC., Fribourg (CH)

( * ) Notice: Subject to any disclaimer, the term of this patent is extended or adjusted under 35 U.S.C. 154(b) by 197 days.

(21) Appl. No.: 17/655,022

(22) Filed: Mar. 16, 2022

(65) Prior Publication Data

US 2022/0304853 A1    Sep. 29, 2022

Related U.S. Application Data

(60) Provisional application No. 63/164,600, filed on Mar. 23, 2021.

(51) Int. Cl.
*A61F 9/008*    (2006.01)
*G16H 40/63*    (2018.01)

(52) U.S. Cl.
CPC .............. *A61F 9/008* (2013.01); *G16H 40/63* (2018.01); *A61F 2009/00844* (2013.01); *A61F 2009/00872* (2013.01); *A61F 2009/00897* (2013.01)

(58) Field of Classification Search
CPC ............ A61F 9/008; A61F 2009/00844; A61F 2009/00872; A61F 2009/00897
USPC ............................................................ 606/4
See application file for complete search history.

(56) References Cited

U.S. PATENT DOCUMENTS

| | | | | |
|---|---|---|---|---|
| 5,616,139 A | * | 4/1997 | Okamoto | A61F 9/008 606/4 |
| 5,755,700 A | * | 5/1998 | Kritzinger | A61F 9/0133 604/35 |
| 6,099,521 A | * | 8/2000 | Shadduck | A61F 9/00802 606/4 |
| 11,672,705 B2 | * | 6/2023 | Gray | A61F 9/00838 606/4 |
| 2003/0153904 A1 | | 8/2003 | Patel | |
| 2004/0243112 A1 | | 12/2004 | Bendett et al. | |
| 2005/0177149 A1 | * | 8/2005 | Peyman | A61F 9/00821 606/27 |
| 2008/0039769 A1 | | 2/2008 | Peyman | |

(Continued)

FOREIGN PATENT DOCUMENTS

WO    2020212199 A1    10/2020

OTHER PUBLICATIONS

Iseli Hans Peter et al. "Clinical Photoablation With a 500-Hz Scanning Spot Excimer Laser", Journal of Refractive Surgery, vol. 20, Nov./Dec. 2004, p. 831.

*Primary Examiner* — Nadia A Mahmood

(57) ABSTRACT

An ophthalmic surgical system for controlling a temperature of a cornea of an eye for a surgical procedure comprises a fluid management system and a computer. The fluid management system manages fluid within a channel structure created in the cornea of the eye. The computer instructs one or more of the controllable components to create the channel structure in the cornea. The channel structure provides a passageway between an interior of the eye and an exterior of the eye, and is proximate to a treatment site. The computer instructs the fluid management system to manage fluid within the channel structure in order to control the temperature of the cornea of the eye.

14 Claims, 4 Drawing Sheets

(56) References Cited

U.S. PATENT DOCUMENTS

2013/0310728 A1* 11/2013 Seiler ................. A61F 9/00804
　　　　　　　　　　　　　　　　　　　604/20
2015/0290030 A1   10/2015 Suckewer et al.
2015/0342784 A1* 12/2015 Seiler ................. A61F 9/00825
　　　　　　　　　　　　　　　　　　　606/4
2016/0175146 A1*  6/2016 Gooding ............... A61F 9/009
　　　　　　　　　　　　　　　　　　　606/4

* cited by examiner

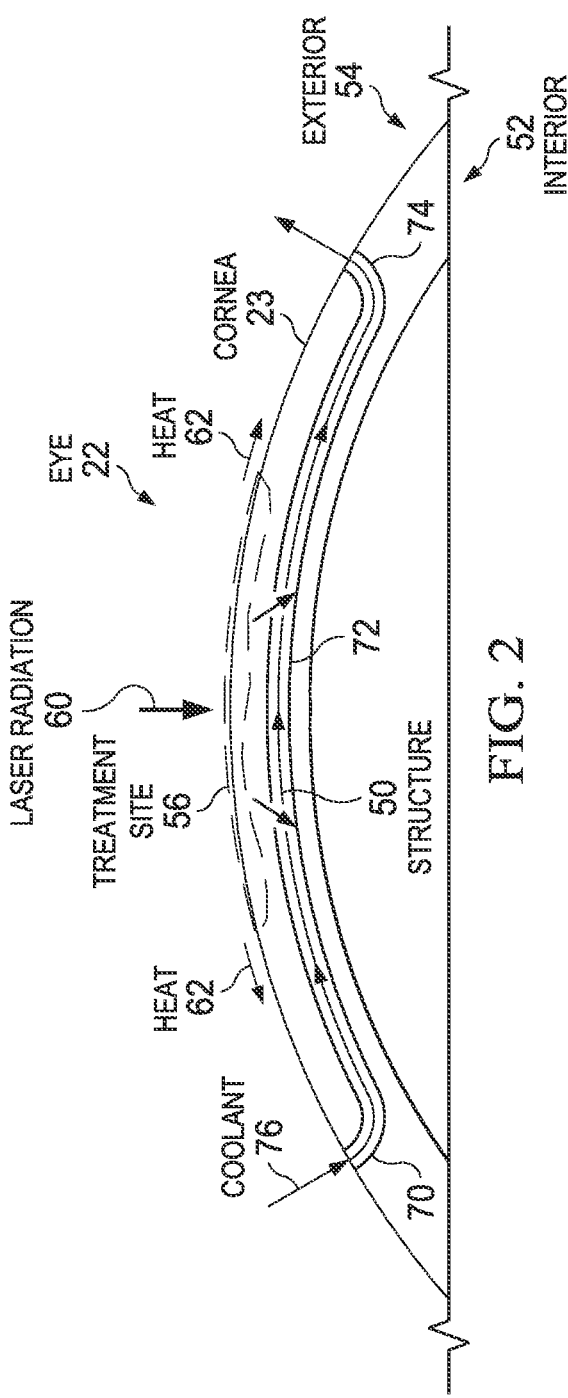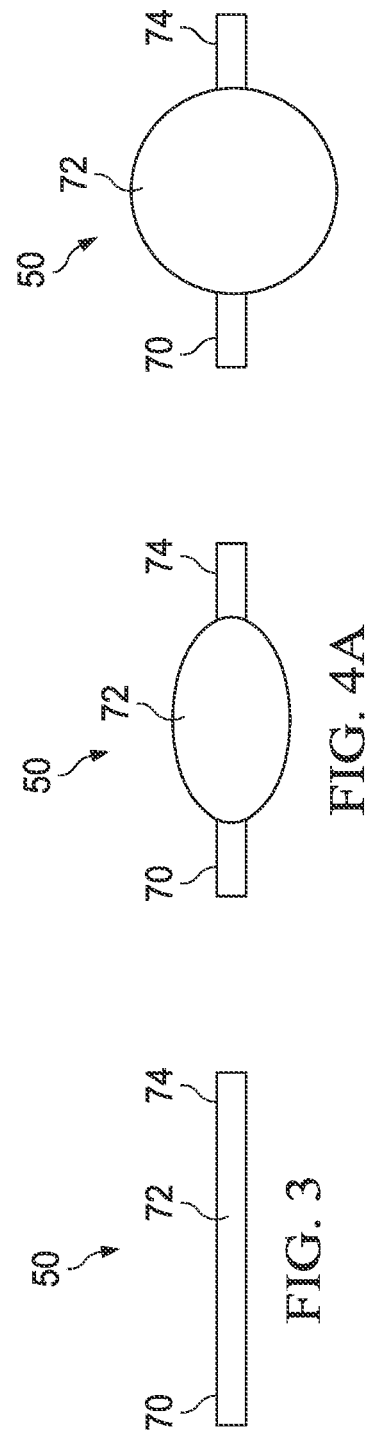

CONTROLLING THE TEMPERATURE OF THE CORNEA DURING OPHTHALMIC SURGERY

TECHNICAL FIELD

The present disclosure relates generally to ophthalmic surgical systems and methods, and more particularly to controlling the temperature of the cornea during ophthalmic surgery.

BACKGROUND

Ophthalmic laser systems are used to perform surgical procedures on eye tissue. In general, a laser delivers laser pulses to the eye tissue. In some procedures, the pulses may create photo-disruptions that form photo-disrupted regions, such as incisions. In other procedures, the pulses may ablate and shape the tissue. During the procedure, the laser pulses increase the temperature of the tissue. This temperature increase may cause damage that negatively affects the healing process and/or treatment outcome.

To avoid such damage, the temperature of the operating room may be lowered or a cooling solution may be applied to the surface of the eye. However, these efforts may fail to provide adequate cooling. Laser pulses may be applied with a lower energy, smaller spot size, or lower frequency to reduce the temperature increase of the tissue. These efforts, however, may extend the treatment time of the procedure.

BRIEF SUMMARY

According to certain embodiments, an ophthalmic surgical system for controlling a temperature of a cornea of an eye for a surgical procedure comprises controllable components, a fluid management system, and a computer. The controllable components comprise a laser source, a scanner, and an objective. The laser source generates a laser beam having ultrashort pulses, where a propagation direction of the laser beam defines a z-axis. The scanner directs a focal point of the laser beam in an xy-plane orthogonal to the z-axis. The objective focuses the focal point towards the cornea of the eye. The fluid management system manages fluid within a channel structure created in the cornea of the eye. The computer instructs one or more of the controllable components to create the channel structure in the cornea. The channel structure provides a passageway between an interior of the eye and an exterior of the eye, and is proximate to a treatment site. The computer instructs the fluid management system to manage fluid within the channel structure in order to control the temperature of the cornea of the eye.

Embodiments may include none, one, some, or all of the following features: The channel structure comprises: a first passage between the exterior of the eye and the interior of the eye; a second passage between the interior of the eye and the exterior of the eye; and an interior portion through the interior of the eye that provides fluid communication between the first passage and the second passage. The interior portion may be posterior to the treatment site, and the first passage, the interior portion, and the second passage may have substantially the same cross-sectional area. The interior portion may be posterior to the treatment site, and may have a substantially elliptical shape in the xy-plane. The interior portion may have a shape designed with respect to the treatment site. The interior portion may have an anterior side and a posterior side, and the anterior side may be connected to the posterior side by tissue at one or more locations. The channel structure comprises: a first passage between the exterior of the eye and the interior of the eye; a second passage between the interior of the eye and the exterior of the eye; and an interior portion through the interior of the eye that provides fluid communication between the first passage and the second passage. The interior portion may comprise channels. One or more of the channels may provide fluid communication between the first passage and the second passage. The channels may be posterior to the treatment site. At least one of the channels may be proximate to a z-position of at least a part of the treatment site. The channel structure comprises: a first passage between the exterior of the eye and an anterior chamber of the eye; and a second passage between the anterior chamber of the eye and the exterior of the eye. The fluid management system may remove aqueous humor from the anterior chamber of the eye. The fluid management system comprises a fluid dispenser configured to dispense fluid into the channel structure. The fluid management system comprises a fluid aspirator configured to aspirate fluid from the channel structure.

According to certain embodiments, a method for controlling a temperature of a cornea of an eye for an ophthalmic surgical procedure, comprises: receiving input describing the surgical procedure; determining a design of a channel structure according to the surgical procedure, the channel structure providing a passageway between an interior of the eye and an exterior of the eye, the channel structure proximate to a treatment site of the surgical procedure; creating the channel structure in the cornea of the eye; performing the surgical procedure; and managing fluid within the channel structure to control the temperature of the cornea of the eye by: dispensing fluid into the channel structure; and aspirating fluid from the channel structure.

Embodiments may include none, one, some, or all of the following features: Dispensing fluid into the channel structure comprises dispensing fluid into the channel structure with a fluid dispenser of a fluid management system. Aspirating fluid from the channel structure comprises aspirating fluid from the channel structure with a fluid aspirator of a fluid management system. The channel structure comprises: a first passage between the exterior of the eye and the interior of the eye; a second passage between the interior of the eye and the exterior of the eye; and an interior portion through the interior of the eye that provides fluid communication between the first passage and the second passage. The channel structure comprises: a first passage between the exterior of the eye and an anterior chamber of the eye; and a second passage between the anterior chamber of the eye and the exterior of the eye. Aspirating fluid from the channel structure may comprise removing aqueous humor from the anterior chamber of the eye.

According to certain embodiments, an ophthalmic surgical system for controlling a temperature of a cornea of an eye for a surgical procedure comprises controllable components, a fluid management system, and a computer. The controllable components comprise a laser source, a scanner, and an objective. The laser source generates a laser beam having ultrashort pulses, where a propagation direction of the laser beam defines a z-axis. The scanner directs a focal point of the laser beam in an xy-plane orthogonal to the z-axis. The objective focuses the focal point towards the cornea of the eye. The fluid management system manages fluid within a channel structure created in the cornea of the eye. The fluid management system comprises a fluid dispenser that dispenses fluid into the channel structure, and a fluid aspirator that aspirates fluid from the channel structure. The computer: instructs one or more of the controllable components to create the channel structure in the cornea, the channel structure providing a passageway between an interior of the eye and an exterior of the eye, the channel structure proximate to a treatment site; and instructs the fluid management system to manage fluid within the channel structure in order to control the temperature of the cornea of the eye. The channel structure is selected from a group consisting of first and second channel structures. The first channel structure comprises: a first passage between the exterior of the eye and the interior of the eye; a second passage between the interior of the eye and the exterior of the eye; and an interior portion through the interior of the eye that provides fluid communication between the first passage and the second passage. The first channel structure is shaped according to a design selected from a group consisting of first through fifth designs. In the first design, the interior portion is posterior to the treatment site, and the first passage, the interior portion, and the second passage have substantially the same cross-sectional area. In the second design, the interior portion is posterior to the treatment site, and the interior portion has a substantially elliptical shape in the xy-plane. In the third design, the interior portion comprises channels, where one or more of the channels provide fluid communication between the first passage and the second passage. In the fourth design, the interior portion has a shape designed with respect to the treatment site. In the fifth design, the interior portion has an anterior side and a posterior side, and the anterior side is connected to the posterior side by tissue at one or more locations. The second channel structure comprises: a first passage between the exterior of the eye and an anterior chamber of the eye; and a second passage between the anterior chamber of the eye and the exterior of the eye.

BRIEF DESCRIPTION OF THE DRAWINGS

FIG. 2 illustrates an example of a channel structure that may be created in a cornea of an eye by the ophthalmic surgical system of FIG. 1;

FIG. 3 illustrates an example of a simple channel structure;

FIGS. 4A and 4B illustrate examples of elliptical interior portions with a substantially elliptical shape;

DESCRIPTION OF EXAMPLE EMBODIMENTS

Figure 1:
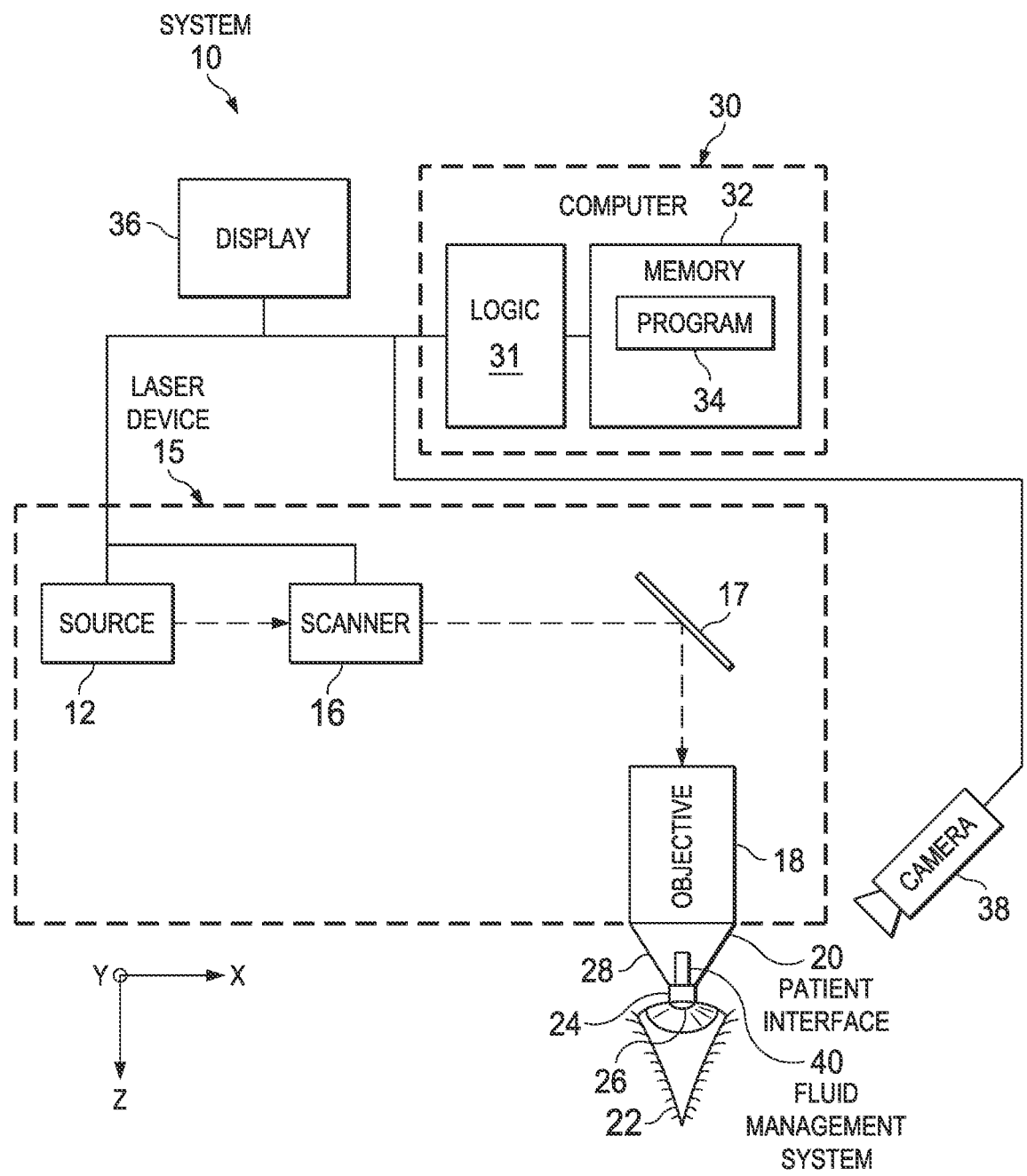
FIG. 1 illustrates an example of an ophthalmic surgical system configured to control the temperature of the cornea of an eye, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

In general, an ophthalmic surgical system performs a laser surgical procedure at a treatment site of a cornea. During the procedure, the pulses increase the temperature of the corneal tissue. The surgical system may control the temperature to avoid heat damage to the tissue without extending treatment time.

FIG. 1 illustrates an example of an ophthalmic surgical system 10 configured to control the temperature of the cornea of an eye 22, according to certain embodiments. In the embodiments, a laser creates a channel structure in the cornea proximate to the treatment site. A fluid management system manages fluid within the channel structure to control the temperature of the cornea. Surgical system 10 may control the temperature to avoid heat damage to the tissue while minimizing or avoiding any extension of treatment time.

In the illustrated example, system 10 includes a laser device 15, a patient interface 20, a camera 38, a fluid management system 40, and a control computer 30, coupled as shown. Laser device 15 includes controllable components, such as a laser source 12, a scanner 16, one or more optical elements 17, and/or a focusing objective 18, controllable by a computer such as computer 30, coupled as shown. Patient interface 20 includes a contact portion 24 (with an abutment face 26) and a sleeve 28 coupled as shown. Computer 30 includes logic 31, a memory 32 (which stores a computer program 34), and a display 36, coupled as shown.

As an overview, ophthalmic surgical system 10 controls the temperature of the cornea of eye 22 during a surgical procedure. Ophthalmic surgical system 10 may perform any suitable surgical procedure, such as corneal refractive surgery or other ophthalmic laser surgery. The surgical procedure may have a treatment pattern, which describes the target locations of the laser pulses in the cornea. The treatment pattern defines the treatment site, i.e., the location of the cornea to be treated by the laser pulses.

According to the overview, laser source 12 can generate a laser beam having ultrashort pulses, where a propagation direction of the laser beam defines a z-axis and/or z-direction. Scanner 16 can direct a focal point of the laser beam in an xy-plane that is orthogonal to the z-axis. Objective 18 can focus the focal point towards the cornea of eye 22. Fluid management system 40 can manage fluid within a channel structure created in the cornea. Computer 30 instructs one or more of the controllable components to create the channel structure in the cornea. The channel structure provides a passageway between the interior and exterior of eye 22, and is proximate to a treatment site. Computer 30 instructs the fluid management system to manage fluid within the channel structure in order to control the temperature of the cornea.

Turning to the parts of system 10, laser source 12 generates a laser beam with ultrashort pulses. An ultrashort pulse refers to a light pulse that has a duration that is less than a nanosecond, such as on the order of picoseconds, femtoseconds, or attoseconds. The laser beam may have any suitable wavelength, such as a wavelength in the range of 300 to 1500 nanometers (nm), e.g., a wavelength in the range of 300 to 650, 650 to 1050, 1050 to 1250, and/or 1250 to 1500 nm, such as 340 to 350 nm, e.g., 347 nm±1 nm. The focal point of the laser beam may create a laser-induced optical breakdown (LIOB) in tissue (e.g., the cornea) to yield a photodisruption in the tissue. The laser beam may be precisely focused to yield precise photodisruptions, which may reduce or avoid unnecessary destruction of other tissue.

Scanner 16 longitudinally and transversely directs the focal point of the laser beam. The longitudinal direction refers to the direction of the laser beam propagation, i.e., the z-direction. Scanner 16 may longitudinally direct the laser beam in any suitable manner. For example, scanner 16 may include a longitudinally adjustable lens, a lens of variable refractive power, or a deformable mirror that can control the z-position of the focal point.

The transverse direction refers to directions orthogonal to the direction of beam propagation, i.e., the x- and y-directions. Scanner 16 may transversely direct the laser beam in any suitable manner. For example, scanner 16 may include a pair of galvanometrically-actuated scanner mirrors that can be tilted about mutually perpendicular axes. As another example, scanner 16 may include an electro-optical crystal that can electro-optically steer the laser beam.

One (or more) optical elements 17 direct the laser beam towards focusing objective 18. An optical element 17 can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical element 17 is a mirror. Focusing objective 18 focuses the focal point of laser beam through the patient interface 20 towards a point of eye 22. In the example, focusing objective 18 is an objective lens, e.g., an f-theta objective.

Patient interface 20 interfaces with the cornea of eye 22 to couple eye 22 to laser device 15. In the example, patient interface 20 has sleeve 28 coupled to contact portion 24. Sleeve 28 detachably couples to focusing objective 18. Contact portion 24 may be translucent or transparent to the laser beam and has an abutment face 26 that interfaces with the cornea. Abutment face 26 may have any suitable shape, e.g., planar, convex, or concave.

Fluid management system 40 manages fluid within a channel structure created in the cornea of eye 22. In certain embodiments, fluid management system 40 includes a fluid dispenser that dispenses fluid into the channel structure, and/or a fluid aspirator that aspirates fluid from the channel structure. The dispenser and aspirator may dock to different channels or may dock to a common channel to dispense and aspirate, respectively, fluid. The dispenser and aspirator may dock to a channel or channels by mechanical or vacuum pressure. Fluid management system 40 may be integrated with any suitable portion of system 10, e.g., speculum, laser head, suction ring or cone of the patient interface, tube system of a cannula, other implementation located near the eye.

In certain embodiments, fluid management system 40 provides a fluid, e.g., a coolant) into a channel structure to cool the tissue. A coolant has a high specific heat capacity. Examples of coolants include cooled liquids (e.g. a balanced salt solution (BSS)), gels, gases, alcohols, or other non-hazardous fluid with suitable flow properties and thermal conductivity.

Camera 38 records images of the movement of eye 22, which includes movement of the marker created in eye 22. Examples of camera 38 include a video, optical coherence tomography (OCT), or eye-tracking camera. Camera 38 delivers image data, which represent recorded images of the eye 22, to computer 30. Computer 30 may use the image data to, e.g., facilitate creation of the channel structure.

Computer 30 controls controllable components (e.g., laser source 12, scanner 16, optical elements 17, and/or focusing objective 18) in accordance with instructions (which may be stored in computer program 34) to photodisrupt corneal tissue to create a channel in the cornea. The channel structure provides a passageway between the interior and exterior of eye 22, and is proximate to the treatment site. "Proximate to" may refer to a distance with a value in the range of greater than 0 to 10, 10 to 100, 100 to 200 and/or 200 to 400 micrometers.

In certain embodiments, the channel structure includes a first passage, a second passage, and an interior portion. The first passage is between the exterior and interior of eye 22, and may be an entrance from the exterior to the interior. The second passage is between the exterior and interior of eye 22, and may be an exit from the interior to the exterior. The interior portion extends through the interior and provides fluid communication between the first and second passages. The interior portion may be posterior to the treatment site, proximate to the z-depth of the treatment site, or partially posterior and partially proximate to the z-depth. Examples of designs of channel structures are described in more detail with reference to FIGS. 3 to 8.

In certain embodiments, computer 30 determines the size and/or shape ("size/shape") of the channel structure in accordance with the surgical procedure. For example, computer 30 may design the size/shape of an interior portion of the channel structure in accordance with the treatment site, which may be defined by the treatment pattern of the procedure. In these cases, the size/shape of the interior portion may: substantially match the size/shape of the treatment site; be slightly larger than that of the treatment site (e.g., extend past a border of the site by less than 200 micrometers); or be slightly smaller than that of the treatment site (e.g., almost reach the border by less than 200 micrometers). Or, the size/shape of the interior portion may match that of, be slightly larger than, or be slightly smaller than the size/shape of the treatment site at some portions, but not at others.

As another example, computer 30 may select a design based on the expected heat generated by the procedure. The heat may be predicted from the treatment pattern of the procedure. Generally, areas with more laser pulses will tend to become hotter. Computer 30 may select a design that allows more and/or faster fluid flow through the channel structure for a procedure that is expected to generate more heat, and may select a design that allows less and/or slower fluid flow through the channel structure for a procedure that is expected to generate less heat. In addition, computer 30 may select a design that allows more and/or faster fluid flow through parts of the channel structure where the procedure is expected to generate more heat, and may select a design that allows less and/or slower fluid flow through parts of the channel structure where the procedure is expected to generate less heat.

Computer 30 instructs fluid management system 40 to manage fluid within the channel structure in order to control the temperature of the cornea. Computer 30 may manage fluid in any suitable manner. In certain embodiments, the flow of cooler fluid into the channel structure and/or the removal of warmer fluid lowers the temperature of the corneal tissue. If the temperature of the tissue needs to be lowered, the amount of cooler fluid flowing into the channel structure is increased (e.g., by initiating or increasing the flow of cooler fluid into the tissue) and/or the amount of warmer fluid removed from channel structure is increased (e.g., by initiating or increasing the flow of warmer fluid from the tissue). In addition, the temperature may be controlled for specific parts of the treatment site. For example, if a particular region of the site is expected to generate more heat, the fluid may be managed to increase flow of cooler fluid and/or removal of warmer fluid in the region.

FIG. 2 illustrates an example of a channel structure 50 that may be created in a cornea 23 of eye 22 by ophthalmic surgical system 10 of FIG. 1. As laser radiation 60 is applied to a laser treatment site 56 of cornea 23, heat 62 is generated at treatment site 56. In the example, channel structure 50 provides a fluid passageway between the interior 52 and exterior 54 of eye 22 and through the interior 52 proximate to laser treatment site 56. In the example, channel structure 50 includes a first passage between exterior 54 and interior 52 (e.g., an entrance 70 from exterior 54 to interior 52); a second passage between exterior 54 and interior 52 (e.g., an exit 74 from interior 52 to exterior 54); and an interior portion 72 through interior 52 and between the first and second passages. As coolant 76 flows through structure 50, heat 62 is carried away from treatment site 56.

FIGS. 3 through 7 illustrate examples of channel structures 50 with various embodiments of interior portion 72. In the examples, channel structures 50 are shown in the xy-plane.

FIG. 3 illustrates an example of a simple channel structure 50. In the example, entrance 70, interior portion 72, and exit 74 have substantially the same cross-sectional area. In certain cases, there is no substantial differences in the cross-sectional area throughout channel structure 50. Interior portion 72 may be posterior to treatment site 56, i.e., at a z-position that is posterior to site 56.

FIGS. 4A and 4B illustrate examples of elliptical interior portions 72 with a substantially elliptical shape (e.g., oval or circle) in the xy-plane. Interior portions 72 may be posterior to treatment site 56, i.e., at a z-position that is posterior to site 56. FIG. 4A illustrates an oval interior portion 72. Oval interior portion 72 may have any suitable dimensions, e.g., a major axis in the range of microns to millimeters (e.g., 100 μm to 10 mm), and a minor axis in the range of microns to millimeters (e.g., 100 μm to 10 mm). FIG. 4B illustrates a circular interior portion 72. Circular interior portion 72 may have any suitable dimensions, e.g., a diameter in the range of microns to millimeters (e.g., 100 μm to 10 mm).

Figure 5:
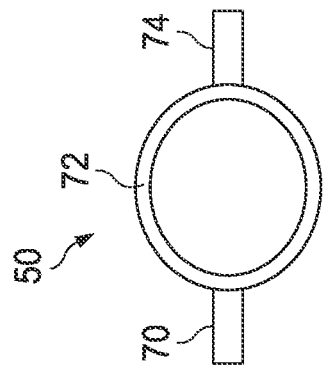
FIG. 5 illustrates an example of an interior portion with tissue connections that connect the anterior and posterior sides of a channel structure.

FIG. 5 illustrates an example of interior portion 72 with tissue connections 80 that connect the anterior and posterior sides of channel structure 50. In the example, interior portion 72 has an anterior side 82 and a posterior side 84. Anterior side 82 is connected to posterior side 84 by one or more tissue connections 80. A tissue connection may be formed at a location by not photodisrupting and/or not manually detaching the sides 82, 84 at the location. Interior portion 72 may be posterior to treatment site 56 or at substantially the same z-position as treatment site 56.

Figure 6:
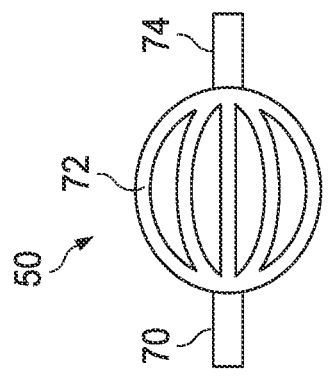
FIG. 6 illustrates an example of an interior portion with multiple channels.

FIG. 6 illustrates an example of interior portion 72 with multiple channels 86. In the example, interior portion 72 comprises a plurality of channels 86. One or more of channels 86 provide fluid communication between entrance 70 and exit 74. In the example, channels 86 are posterior to the treatment site (i.e., at a z-position that is posterior to site 56).

Figure 7:
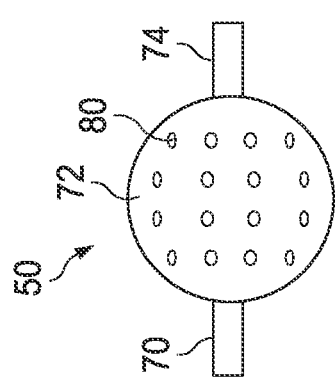
FIG. 7 illustrates an example of an interior portion with two channels that provide fluid communication between the entrance and exit.

FIG. 7 illustrates an example of interior portion 72 with two channels 86 that provide fluid communication between entrance 70 and exit 74. In the example, channels 86 are at substantially the same z-position as treatment site 56 and may surround site 56.

Figure 8:
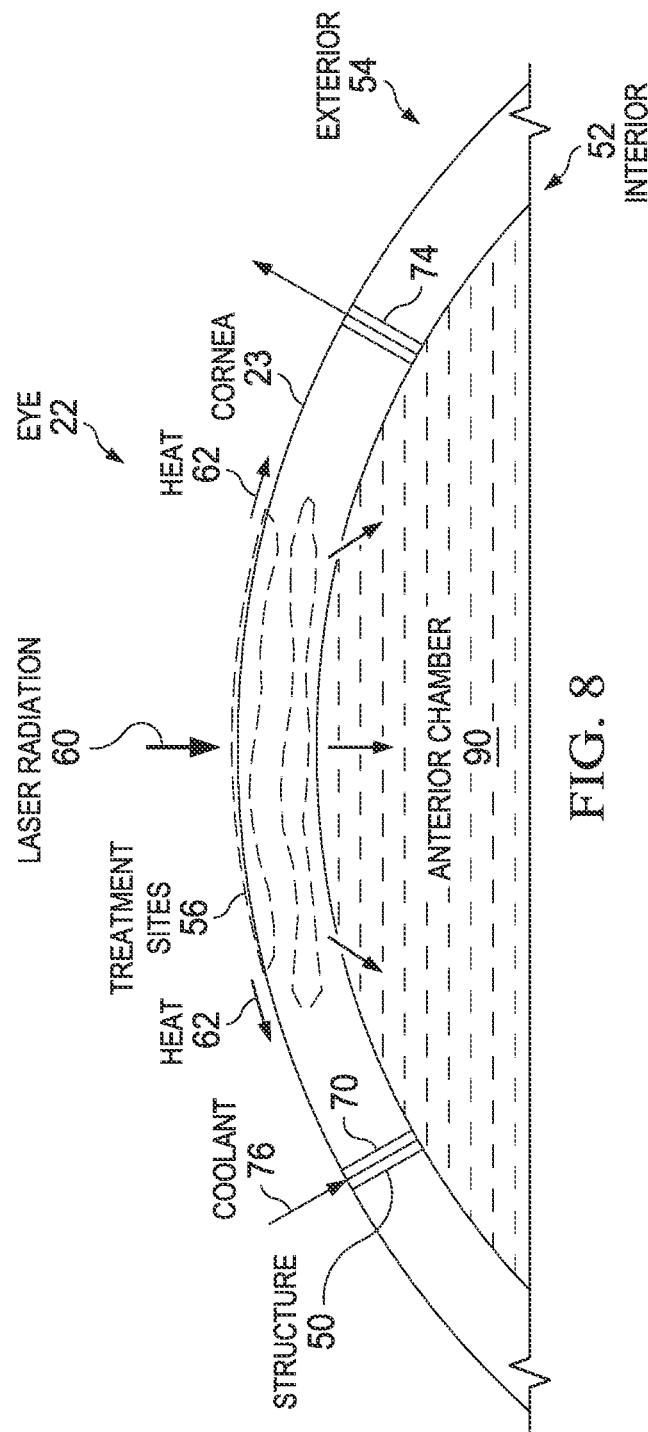
FIG. 8 illustrates another example of a channel structure that may be created in the cornea of an eye by the ophthalmic surgical system of FIG. 1.

FIG. 8 illustrates another example of a channel structure 50 that may be created in a cornea 23 of eye 22 by ophthalmic surgical system 10 of FIG. 1. As laser radiation 60 is applied to a laser treatment site 56 of cornea 23, heat 62 flows away from site 56. In the example, channel structure 50 provides a fluid passageway between the anterior chamber 90 of eye 22 and exterior 54 of eye 22 proximate to laser treatment site 56. In the example, channel structure 50 includes a first passage (e.g., an entrance 70 from exterior 54 to anterior chamber 90) and a second passage (e.g., an exit 74 from anterior chamber 90 to exterior 54). Fluid management system 40 provides a coolant 76 into channel structure 50 and/or extracts coolant 76 and/or aqueous humor to cool the tissue.

Figure 9:
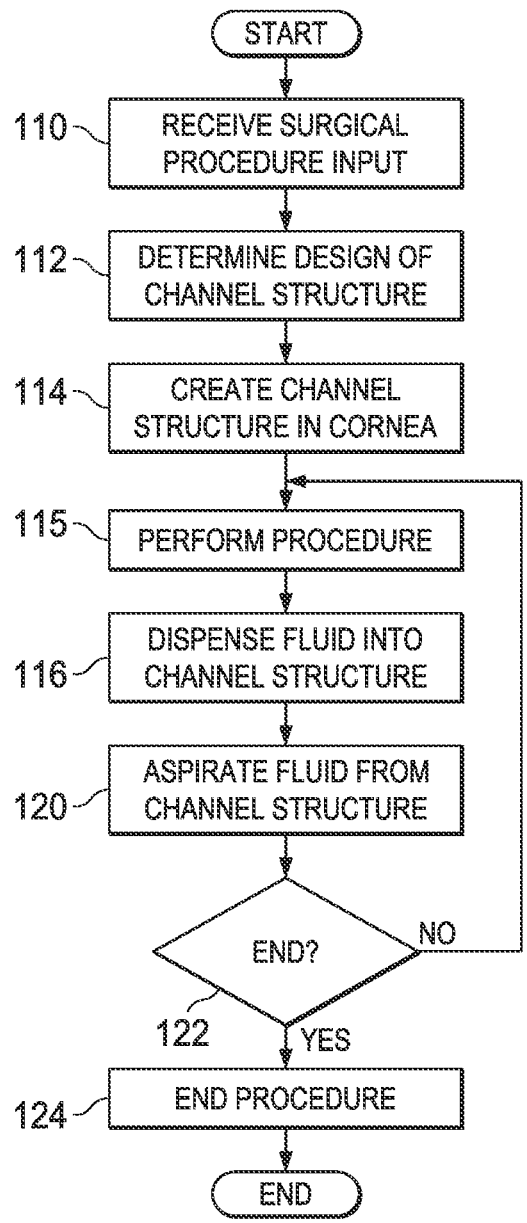
FIG. 9 illustrates an example of a method for controlling the temperature of the cornea of an eye during an ophthalmic surgical procedure, which may be performed by the ophthalmic surgical system of FIG. 1.

FIG. 9 illustrates an example of a method for controlling the temperature of the cornea of an eye 22 during an ophthalmic surgical procedure, which may be performed by ophthalmic surgical system 10 of FIG. 1. The method starts at step 110, where computer 30 receives input describing the surgical procedure. The input may include the type of procedure and the treatment pattern.

The design of the channel structure is determined at step 112. The design may be determined according to the surgical procedure, e.g., the size/shape of the treatment site and/or the predicted heat generated by the treatment. In certain embodiments, the channel structure includes a first passage and a second passage. The first passage is between the exterior and interior of eye 22, and may be an entrance from the exterior to the interior. The second passage is between the exterior and interior of eye 22, and may be an exit from the interior to the exterior. In certain embodiments, the channel structure also includes an interior portion. The interior portion extends through the interior and provides fluid communication between the first and second passages. The channel structure is created in the cornea according to the design at step 114.

Computer 30 performs the surgical procedure according to the treatment pattern at step 115. For example, corneal refractive surgery is performed. Fluid is dispensed into the channel structure at step 116 by, e.g., a fluid dispenser. The fluid may comprise, e.g., a coolant. Fluid is aspirated from the channel structure at step 120 by, e.g., a fluid aspirator.

The procedure may be at its end at step 122. If the procedure is not at its end, the method returns to step 115, where computer 30 continues to perform the surgical procedure. If the procedure is at its end, the method proceeds to step 124 to end the procedure. The method then ends.

A component (such as computer 30) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface (e.g., a Graphical User Interface (GUI)) is a type of interface that a user can utilize to interact with a computer. Examples of user interfaces include a display, touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic surgical system for controlling a temperature of a cornea of an eye for a surgical procedure, comprising:
   a plurality of controllable components comprising:
      a laser source configured to generate a laser beam having a plurality of ultrashort pulses, a propagation direction of the laser beam defining a z-axis;
      a scanner configured to direct a focal point of the laser beam in an xy-plane orthogonal to the z-axis; and
      an objective configured to focus the focal point towards the cornea of the eye;
   a fluid management system configured to manage fluid within a channel structure created within the cornea of the eye; and
   a computer configured to:
      instruct one or more of the controllable components to create the channel structure within the cornea, the channel structure providing a passageway between an interior of the eye and an exterior of the eye, the channel structure comprising a first passage between the exterior of the eye and the interior of the eye, a second passage between the interior of the eye and the exterior of the eye, and an interior passage within the cornea of the eye that provides fluid communication between the first passage and the second passage, the interior passage comprising an elliptical channel having an elliptical shape in the xy-plane, the elliptical channel having a first channel side, the elliptical channel having a second channel side, the first channel side opposite the second channel side in the xy-plane, the first channel side and the second channel side conforming to an ellipse in the xy-plane, the channel structure proximate to a treatment site; and
      instruct the fluid management system to manage fluid within the channel structure in order to control the temperature of the cornea of the eye.

2. The ophthalmic surgical system of claim 1, wherein:
   the interior passage is posterior to the treatment site; and
   the first passage, the interior passage, and the second passage have the same cross-sectional area.

3. The ophthalmic surgical system of claim 1, wherein:
   the interior passage is posterior to the treatment site.

4. The ophthalmic surgical system of claim 1, wherein the interior passage comprises a plurality of channels, one or more of the channels providing fluid communication between the first passage and the second passage.

5. The ophthalmic surgical system of claim 1, wherein the interior passage comprises a plurality of channels, one or more of the channels providing fluid communication between the first passage and the second passage, the channels posterior to the treatment site.

6. The ophthalmic surgical system of claim 1, wherein the interior passage comprises a plurality of channels, one or more of the channels providing fluid communication between the first passage and the second passage, at least one of the channels proximate to a z-position of at least a part of the treatment site.

7. The ophthalmic surgical system of claim 1, wherein the interior passage has a shape designed with respect to the treatment site.

8. The ophthalmic surgical system of claim 1, wherein:
   the interior passage has an anterior side and a posterior side; and
   the anterior side is connected to the posterior side by tissue at one or more locations.

9. The ophthalmic surgical system of claim 1, wherein the fluid management system comprises a fluid dispenser configured to dispense fluid into the channel structure.

10. The ophthalmic surgical system of claim 1, wherein the fluid management system comprises a fluid aspirator configured to aspirate fluid from the channel structure.

11. A method for controlling a temperature of a cornea of an eye for an ophthalmic surgical procedure, comprising:
   receiving input describing the surgical procedure;
   determining a design of a channel structure according to the surgical procedure, the channel structure providing a passageway between an interior of the eye and an exterior of the eye, the channel structure proximate to a treatment site of the surgical procedure;
   creating the channel structure within the cornea of the eye, the channel structure comprising a first passage between the exterior of the eye and the interior of the eye, a second passage between the interior of the eye and the exterior of the eye, and an interior passage within the cornea of the eye that provides fluid communication between the first passage and the second passage, the interior passage comprising an elliptical channel having an elliptical shape in an xy-plane, the elliptical channel having a first channel side, the elliptical channel having a second channel side, the first channel side opposite the second channel side in the xy-plane, the first channel side and the second channel side conforming to an ellipse in the xy-plane;
performing the surgical procedure; and
managing fluid within the channel structure to control the temperature of the cornea of the eye by:
dispensing fluid into the channel structure; and
aspirating fluid from the channel structure.

12. The method of claim 11, the dispensing fluid into the channel structure comprising:
dispensing fluid into the channel structure with a fluid dispenser of a fluid management system.

13. The method of claim 11, the aspirating fluid from the channel structure comprising:
aspirating fluid from the channel structure with a fluid aspirator of a fluid management system.

14. An ophthalmic surgical system for controlling a temperature of a cornea of an eye for a surgical procedure, comprising:
a plurality of controllable components comprising:
a laser source configured to generate a laser beam having a plurality of ultrashort pulses, a propagation direction of the laser beam defining a z-axis;
a scanner configured to direct a focal point of the laser beam in an xy-plane orthogonal to the z-axis; and
an objective configured to focus the focal point towards the cornea of the eye;
a fluid management system configured to manage fluid within a channel structure created within the cornea of the eye, the fluid management system comprising:
a fluid dispenser configured to dispense fluid into the channel structure; and
a fluid aspirator configured to aspirate fluid from the channel structure; and
a computer configured to:
instruct one or more of the controllable components to create the channel structure within the cornea, the channel structure providing a passageway between an interior of the eye and an exterior of the eye, the channel structure proximate to a treatment site; and
instruct the fluid management system to manage fluid within the channel structure in order to control the temperature of the cornea of the eye, the channel structure comprising:
a first channel structure comprising:
a first passage between the exterior of the eye and the interior of the eye;
a second passage between the interior of the eye and the exterior of the eye; and
an interior passage within the cornea of the eye that provides fluid communication between the first passage and the second passage, the interior passage comprising an elliptical channel having an elliptical shape in the xy-plane, the elliptical channel having a first channel side, the elliptical channel having a second channel side, the first channel side opposite the second channel side in the xy-plane, the first channel side and the second channel side conforming to an ellipse in the xy-plane, wherein the first channel structure is shaped according to a design selected from a group consisting of:
a first design wherein: the interior passage is posterior to the treatment site; and the first passage, the interior passage, and the second passage have the same cross-sectional area;
a second design wherein: the interior passage is posterior to the treatment site;
a third design wherein: the interior passage comprises a plurality of channels, one or more of the channels providing fluid communication between the first passage and the second passage;
a fourth design wherein: the interior passage has a shape designed with respect to the treatment site; and
a fifth design wherein: the interior passage has an anterior side and a posterior side; and the anterior side is connected to the posterior side by tissue at one or more locations.

\* \* \* \* \*